United States Patent [19]

Effland et al.

[11] Patent Number: 5,276,156
[45] Date of Patent: Jan. 4, 1994

[54] N-(HALOPYRIDIN-4-YL)-N-SUBSTITUTED COMPOUNDS AS INTERMEDIATES IN THE PREPARATION OF 1-(PYRIDO[3,4-B]-1,4-OXAZINYL-4-YL-1H-INDOLES

[75] Inventors: Richard C. Effland, Bridgewater; Larry Davis, Sergeantsville; Gordon E. Olsen, Somerset, all of N.J.

[73] Assignee: Hoechst-Roussel Pharmaceuticals Incorporated, Somerville, N.J.

[21] Appl. No.: 976,778

[22] Filed: Nov. 16, 1992

Related U.S. Application Data

[62] Division of Ser. No. 684,758, Apr. 15, 1991, Pat. No. 5,214,038.

[51] Int. Cl.$^5$ .................... C07D 401/12; A61K 31/44
[52] U.S. Cl. .................... 546/273; 546/147; 546/194; 540/597; 544/131; 544/364
[58] Field of Search ............... 540/597; 544/124, 364, 544/131; 546/147, 194, 273

[56] References Cited

U.S. PATENT DOCUMENTS 4,880,822 11/1989 Effland et al. .................... 546/273
4,970,218 11/1990 Effland et al. .................... 546/273

Primary Examiner—John M. Ford
Assistant Examiner—Philip Datlow
Attorney, Agent, or Firm—Elliott Korsen

[57] ABSTRACT

This invention relates to 1-(pyrido[3,4-b]-1,4-oxazinyl-4-yl)-1H-indoles of the formula

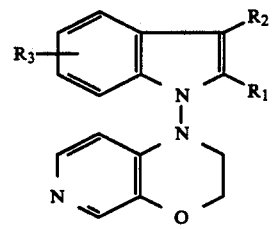

where $R_1$–$R_3$ are as defined herein which are useful for alleviation of depression and various memory dysfunction characterized by a cholinergic or adrenergic deficit. This invention also relates to intermediate compounds of the formula

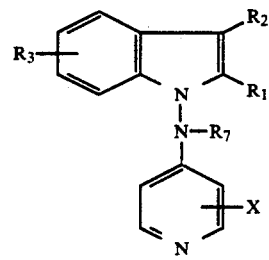

where $R_1$, $R_2$, $R_3$, $R_7$ and X are as defined herein.

4 Claims, No Drawings

N-(HALOPYRIDIN-4-YL)-N-SUBSTITUTED COMPOUNDS AS INTERMEDIATES IN THE PREPARATION OF 1-(PYRIDO[3,4-B]-1,4-OXAZINYL-4-YL-1H-INDOLES

This is a division of application Ser. No. 684,758, filed Apr. 15, 1991, now U.S. Pat. No. 5,214,038.

This invention relates to compound I of the formula

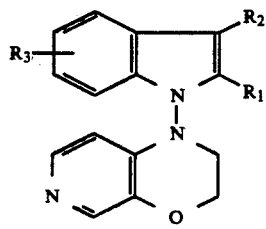

wherein $R_1$ is hydrogen or loweralkyl;

$R_2$ is hydrogen or loweralkyl; and $R_3$ is hydrogen, loweralkyl, halogen, nitro, amino, hydroxy, loweralkoxy, benzyloxy or

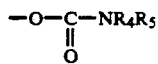

where $R_4$ is hydrogen or loweralkyl and $R_5$ is loweralkyl, aryl, arylloweralkyl or $R_4$ and $R_5$ taken together form a heterocyclic ring selected from the group consisting of

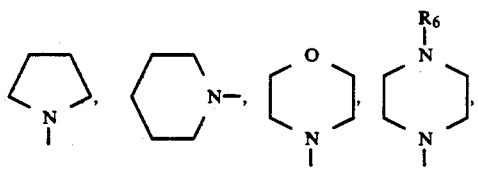

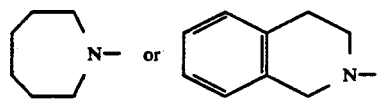

wherein $R_6$ is hydrogen, loweralkyl, aryl or arylloweralkyl; or a pharmaceutically acceptable addition salt thereof.

The compounds of this invention are useful for alleviating depression or various memory dysfunctions characterized by a cholinergic or adrenergic deficit.

This invention also relates to compounds of the formula

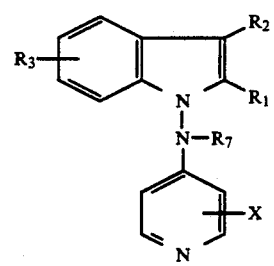

wherein $R_1$, $R_2$ and $R_3$ are as previously defined, X is halogen and $R_7$ is $(CH_2)_2OH$,

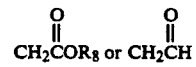

where $R_8$ is hydrogen or loweralkyl. These compounds are useful as intermediates in the preparation of the target compounds.

Unless otherwise stated or indicated, the following definitions shall apply throughout the specification and the appended claims.

The term loweralkyl shall mean a straight or branched alkyl group having from 1 to 7 carbon atoms, e.g., methyl, ethyl, n-propyl, isopropyl, n-butyl, isobutyl, sec-butyl, t-butyl and straight and branched-chain pentyl, hexyl and heptyl.

The term halogen shall mean fluorine, chlorine, bromine or iodine.

The term aryl shall mean a phenyl group substituted with 0, 1 or 2 substituents each of which being independently loweralkyl, loweralkoxy, halogen or trifluoromethyl.

Throughout the specification and appended claims, a given chemical formula or name shall encompass all stereo, optical, geometrical and tautomeric isomers where such isomers exist.

The compounds of the invention are prepared in the following manner. The substituents $R_1$, $R_2$, $R_3$, $R_4$, and $R_5$ shall have the respective meanings given above unless otherwise stated or indicated.

PREPARATION

Compound II of the formula

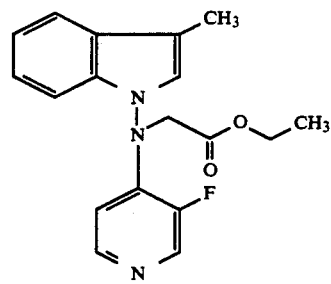

is reacted with lithium aluminum hydride or other suitable reducing agent in a standard reduction to yield Compound III of the formula

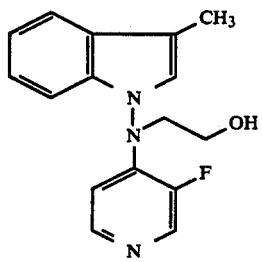

(III)

This reaction is typically conducted in an ethereal solvent such as tetrahydrofuran or ether at a temperature of between about 0° C. and 10° C. for 1 to 4 hours.

Compound II is prepared by the reaction of a compound of the formula IIa

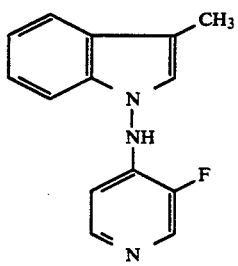

(IIa)

with ethyl chloroacetate in the presence of a strong base such as sodium hydride.

Compound III is subsequently cyclized using a strong base such as sodium hydride or potassium t-butoxide to produce Compound I where $R_3$ is hydrogen.

This reaction typically takes place in a polar aprotic solvent such as dimethylformamide, dimethylacetamide, N-methyl-2-pyrrolidone, hexamethylphosphoramide or dimethyl sulfoxide at a temperature of between about 25° C. to 100° C. for about 1 to 10 hours.

Compounds where $R_3 \neq$ hydrogen can be prepared in the following manner.

Compound IV of the formula

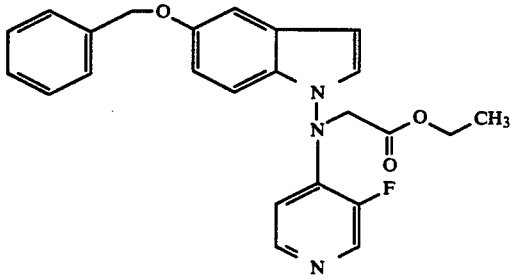

(IV)

is reduced in a manner similar to that discussed above with lithium aluminum hydride or other suitable reducing agent to afford Compound V of the formula

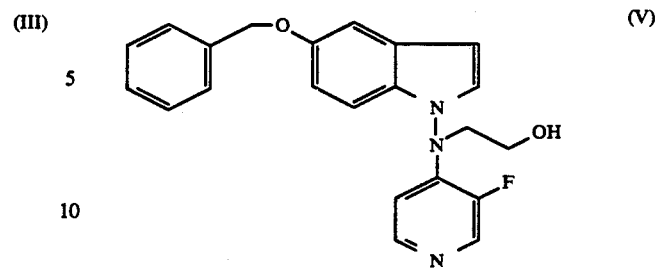

(V)

Compound V is cyclized in a manner similar to that described above to afford Compound VI of the invention of the formula

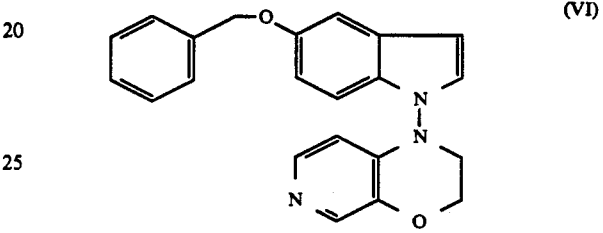

(VI)

Compound VI is subjected to catalytic hydrogenolysis to afford Compound VII of the invention of the formula

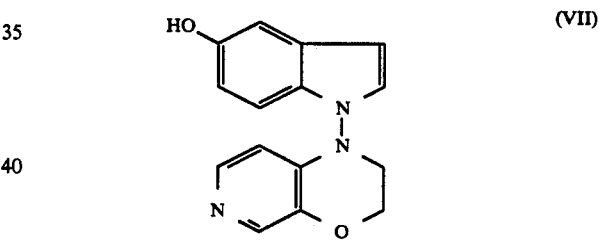

(VII)

The hydrogenolysis is typically conducted with a noble metal catalyst, such as platinum or palladium on carbon in a loweralkanol solvent such as ethanol or isopropanol at a temperature of between about 25° C. to 80° C.

Compound VII is reacted with an isocyanate of the formula $R_5$-NCO wherein $R_5$ is loweralkyl, aryl or arylloweralkyl to afford Compound I wherein $R_3$ is

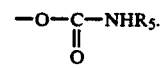

This reaction typically takes place in the presence of a base such as potassium carbonate in a solvent such as tetrahydrofuran at a temperature of between about 0° C. to 50° C. for 1 to 24 hours.

To prepare Compound I where $R_4$ and $R_5$ taken together form a heterocyclic ring, Compound VII is reacted with compounds selected from the group consisting of

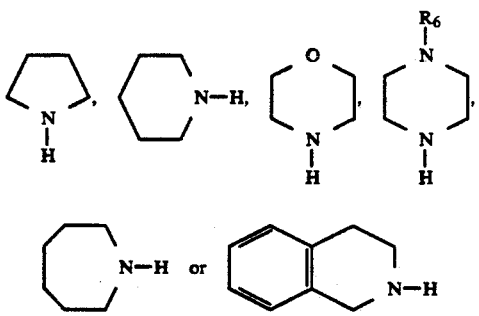

in the presence of carbonyldiimidazole. This reaction typically takes place in an ethereal solvent such as tetrahydrofuran or dioxane at a temperature of about 0° to 70° C. for 1 to 24 hours.

The compounds of Formula I of the present invention are useful for the treatment of various memory dysfunctions characterized by a decreased cholinergic or adrenergic function, such as Alzheimer's disease, and for alleviating depression.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents
  1. 0.05M Phosphate buffer, pH 7.2
    (a) 6.85 g $NaH_2PO_4 \cdot H_2O$/100 ml distilled $H_2O$
    (b) 13.40 g $Na_2HPO_4 \cdot 7H_2O$/100 ml distilled $H_2O$
    (c) add (a) to (b) until pH reaches 7.2
    (d) Dilute 1:10
  2. Substrate in buffer
    (a) 198 mg acetylthiocholine chloride (10 mM)
    (b) q.s. to 100 ml with 0.05M phosphate buffer, pH 7.2 (reagent 1)
  3. DTNB in buffer
    (a) 19.8 mg 5,5-dithiobisnitrobenzoic acid (DTNB) (0.5 mM)
    (b) q.s. to 100 ml with 0.05M phosphate buffer, pH 7.2 (reagent 1)
  4. A 2 mM stock solution of the test drug is made up in a suitable solvent and q.s. to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2, using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)
Program #6 Kindata:
Source-Vis
Wavelength-412 nm
Sipper-none
Cuvettes-2 ml cuvettes using auto 6-sampler
Blank-1 for each substrate concentration
Interval time-15 seconds (15 or 30 seconds for kinetics)
Total time-5 minutes (5 or 10 minutes for kinetics)
Plot-yes
Span-autoscale
Slope-increasing
Results-yes (gives slope)
Factor-1

Reagents are added to the blank and sample cuvettes as follows:

| Blank: | 0.8 ml Phosphate Buffer/DTNB |
| | 0.8 ml Buffer/Substrate |
| Control: | 0.8 ml Phosphate Buffer/DTNB/Enzyme |
| | 0.8 ml Phosphate Buffer/Substrate |
| Drug: | 0.8 ml Phosphate Buffer/DTNB/Drug/Enzyme |
| | 0.8 ml Phosphate Buffer/Substrate |

Blank values are determined for each run to control non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration $$\left(\frac{\text{slope control} - \text{slope drug}}{\text{slope control}}\right)(100)$$

Results of this assay for some of the compounds of this invention and physostigmine (reference compound) are presented in Table 1.

TABLE 1

| Compound | Inhibitory Concentration ($\mu$M) Brain AChE |
|---|---|
| 1-(Pyrido[3,4-b]-1,4-oxazin-4-yl)-1H-indol-5-yl methylcarbamate | 0.054 |
| Physostigmine | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before-re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c.) | % of Animals with Scopolamine Induced Memory Deficit Reversal |
|---|---|---|
| 1-(Pyrido-[3,4-b]-1,4-oxazin-4-yl)-1H-indol-5-yl methylcarbamate | 0.01 | 27% |
| | 0.03 | 20% |
| | 0.10 | 33% |
| Tacrine | 0.63 | 13% |
| Pilocarpine | 5.0 | 13% |

These compounds are administered to a subject requiring memory enhancement as an effective oral, parenteral or intravenous dose of from about 1 to 100 mg/kg of body weight per day. A particularly effective amount is about 10 mg/kg of body weight per day. It is to be understood that for any particular subject, specific dosage regimens should be adjusted according to the individual need and the professional judgment of the person administering or supervising the administration of the aforesaid compound. It is to be further understood that the dosages set forth herein are exemplary only and do not, to any extent, limit the scope or practice of the invention.

$^3$H-Norepinephrine Uptake in Rat Whole Brain Synaptosomes

This assay is used as a biochemical screen for compounds that enhance adrenergic mechanism by blocking norepinephrine uptake.

The neuronal re-uptake mechanism for norepinephrine (NE) is the most important physiological means for inactivating NE by removing the transmitter from the synaptic cleft. NE uptake is accomplished by a saturable, stereospecific, high affinity, sodium dependent, active transport system; which has been shown to exist in both peripheral and central nervous system tissue. NE uptake is potently inhibited by cocaine, phenethylamines and tricyclic antidepressants. It is also inhibited by ouabain, metabolic inhibitors and phenoxybenzamine. The inhibition of NE uptake by clinically effective tricyclic antidepressants is an important link in the catecholamine hypothesis of affective disorders and extensive structure activity relationships for NE uptake have been worked out.

There are large regional variations in NE uptake which correlate with the endogenous levels of NE. The hypothalamus shows the highest level of NE and the greatest uptake. Synaptosomal $^3$H-NE uptake is a useful marker for the integrity of noreadrenergic neurons, after lesioning experiments, as well as any assay for compounds which potentiate the action of NE by blocking the reuptake mechanism.

Procedure

A. Animals: Male CR Wistar rats (100–125 g).
B. Reagents
1. Krebs-Henseleit Bicarbonate Buffer, pH 7.4 (KHBB)

Make a 1 liter batch, containing the following salts.

| | grams/L | mM |
|---|---|---|
| NaCl | 6.92 | 118.4 |
| KCl | 0.35 | 4.7 |
| MgSO$_4$.7H$_2$O | 0.29 | 2.2 |
| NaHCO$_3$ | 2.10 | 24.9 |
| CaCl$_2$ | 0.14 | 1.3 |
| Prior to use add: | | |
| Dextrose | 2 mg/ml | 11.1 |
| Iproniazid phosphate | 0.30 mg/ml | 0.1 |

Aerate for 60 min. with 95% O$_2$/5% CO$_2$, check pH (7.4±0.1).

2. 0.32M Sucrose: 21.9 g of sucrose, Q.S. to 200 ml.

3. A 0.1 mM stock solution of L(-)-Norepinephrine bitartrate is made up in 0.01N HCl. This is used to dilute the specific activity of radiolabeled NE.

4. Levo-[Ring-2,5,6-$^3$H]-Norepinephrine (40–50 Ci/mmol) is obtained from New England Nuclear.

The final desired concentration of $^3$H-NE in the assay is 50 nM. The dilution factor is 0.8; therefore the KHBB is made up to contain 62.5 nM [$^3$H]-NE. Add to 100 ml of KHBB:

A. 59.4 $\mu$l of 0.1 mM NE = 59.4 nM
*B. 0.31 nmoles of $^3$H-NE = 3.1 nM

-continued

| | |
|---|---|
| | 62.5 nM |

*Calculate volume added from the specific activity of $^3$H-NE.

For most assays, a 1 mM stock solution of the test compound is made up in suitable solvent and serially diluted such that the final concentration in the assay ranges from $2\times10^{-8}$ to $2\times10^{-5}$M. Seven concentrations are used for each assay. Higher or lower concentrations may be used depending on the potency of the test compound.

C. Tissue Preparation

Male Wistar rats are decapitated and brains rapidly removal. Either whole brain minus cerebella or hypothalamus is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min at 0°–4° C. The supernatant ($S_1$) is decanted and is used for uptake experiments.

D. Assay

| | |
|---|---|
| 800 μl | KHBB containing [$^3$H]-NE |
| 20 μl | Vehicle or appropriate drug concentration |
| 200 μl | Tissue suspension |

Tubes are incubated at 37° C. under a 95% $O_2$/5% $CO_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. Inhibitory concentration ($IC_{50}$) values are derived from log-probit analysis. Results of this assay are presented in Table 3.

TABLE 3

| Compound | $IC_{50}$ (μM) |
|---|---|
| 4-(3-Methyl-1H-indol-1-yl)-pyrido[3,4-b]-1,4-oxazine | 6.0 |
| Amitriptyline (reference) | 7.7 |
| Nortriptyline (reference) | 4.0 |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel TM, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:

N-(3-fluoropyridin-4-yl)-N-(3-methyl-1H-indol-1-yl)-2-aminoethanol;

N-(3-fluoropyridin-4-yl)-N-(1H-indol-1-yl)-2-aminoethanol;

(4-(3-methyl-1H-indol-1-yl)-pyrido[3,4-b]-1,4-oxazine;

N-(3-Fluoro-4-pyridinyl)-N-(5-benzyloxy-1H-indol-1-yl)-2-aminoethanol;

4-(1H-indol-1-yl)-pyrido[3,4-b]-1,4-oxazine;

4-(5-benzyloxy-1H-indol-1-yl)-pyrido[3,4-b]-1,4-oxazine;

1-(pyrido-[3,4-b]-1,4-oxazin-4-yl)-1H-indol-5-ol;

1-(pyrido-[3,4-b]-1,4-oxazin-4-yl)-1H-indol-5-yl methylcarbamate;

1-(pyrido-[3,4-b]-1,4-oxazin-4-yl)-2,3-dimethyl-1H-indol-5-yl heptylcarbamate;

1-(pyrido-[3,4-b]-1,4-oxazin-4-yl)-1H-indol-5-yl 1,2,3,4-tetrahydroisoquinolylcarbamate;

1-(pyrido-[3,4-b]-1,4-oxazin-4-yl)-1H-indol-5-yl isopropylcarbamate;

1-(pyrido-[3,4-b]-1,4-oxazin-4-yl)-1H-indol-5-yl phenylmethylcarbamate;

1-(pyrido-[3,4-b]-1,4-oxazin-4-yl)-3-ethyl-1H-indol-5-yl piperidinylcarbamate;

1-(pyrido-[3,4-b]-1,4-oxazin-4-yl)-1H-indol-5-yl morphinlinylcarbamate;

1-(pyrido-[3,4-b]-1,4-oxazin-4-yl)-1H-indol-5-yl 4-methylpiperazinylcarbamate;

1-(pyrido-[3,4-b]-1,4-oxazin-4-yl)-1H-indol-5-yl 4-phenylmethylpiperazinylcarbamate;

N-(3-Fluoro-4-pyridinyl)-N-(1H-indol-1-yl)glycine ethyl ester;

N-(3-Fluoropyridin-4-yl)-N-(1H-indol-1-yl)-2-aminoethanol;

4-(1H-indol-1-yl)-pyrido[3,4-b]-1,4-oxazine;

N-(3-Chloro-4-pyridinyl)-N-(5-benzyloxy-1H-indol-1-yl)glycine ethyl ester;

N-(3-Chloro-4-pyridinyl)-N-(5-benzyloxy-1H-indol-1-yl)-2-aminoethanol;

N-(3-Fluoro-4-pyridinyl)-N-(5-benzyloxy-2-methyl-1H-indol-1-yl)glycine ethyl ester;

N-(3-Fluoro-4-pyridinyl)-N-(5-benzyloxy-2-methyl-1H-indol-1-yl)-2-aminoethanol;

4-(5-Benzyloxy-2-methyl-1H-indol-1-yl)-pyrido[3,4-b]-1,4-oxazine;

2-Methyl-1-(pyrido[3,4-b]-1,4-oxazin-4-yl)-1H-indol-5-ol;

2-Methyl-1-(pyrido[3,4-b]-1,4-oxazin-4-yl)-1H-indol-5-yl methylcarbamate;

2-Methyl-1-(pyrido[3,4-b]-1,4-oxazin-4-yl)-1H-indol-5-yl phenylmethylcarbamate;

N-(3-Fluoro-4-pyridinyl)-N-(5-methoxy-1H-indol-1-yl)-2-aminoethanol;

4-(5-Methoxy-1H-indol-1-yl)-pyrido[3,4-b]-1,4-oxazine;

N-(3-Fluoro-4-pyridinyl)-N-(5-methyl-1H-indol-1-yl)-2-aminoethanol;

4-(5-Methyl-1H-indol-1-yl)-pyrido[3,4-b]-1,4-oxazine;

N-(3-Fluoro-4-pyridinyl)-N-(6-chloro-1H-indol-1-yl)-2-aminoethanol; and 4-(6-Chloro-1H-indol-1-yl)-pyrido[3,4-b]-1,4-oxazine.

The following examples are for illustrative purposes and are not to be construed as limiting the invention disclosed herein. All temperatures are given in degrees centigrade (°C.) unless indicated otherwise.

EXAMPLE 1a

N-(3-Fluoro-4-pyridinyl)-3-methyl-1H-indol-1-amine

To 200 ml isopropanol was added 4-chloro-3-fluoropyridine hydrochloride (10 g) and 3-methyl-1H-indole-1-amine (5.9 g). The mixture was stirred at 90° C. for four hours, cooled; then poured into 500 ml iced-water, pH adjusted to 10 with $Na_2CO_3$ solution, then extracted with ethyl acetate. The organic layer was washed with water, then dried (saturated NaCl, anhydrous $MgSO_4$). After filtering, the solvent was evaporated to an oil, which was eluted on a silica gel column with $CH_2Cl_2$ (DCM) then with ether:petroleum ether (1:1) via flash chromatography. The desired fractions were combined then evaporated to yield 6.2 g of a solid, m.p. 45° C. A sample of this material was recrystallized from isopropyl ether/hexanes (1:1) to give a solid, m.p. 141°–142° C.

Analysis: Calculated for $C_{14}H_{12}FN_3$: 69.69% C, 5.02% H, 17.42% N. Found: 69.52% C, 5.01% H, 17.57% N.

EXAMPLE 1b

N-(3-Fluoro-4-pyridinyl)-N-(3-methyl-1H-indol-1-yl)glycine ethyl ester

To a suspension of NaH (60% in oil, 1.48 g) in 10 ml of dimethylformamide (DMF) at ice bath temperature was added dropwise a solution of N-(3-fluoro-4-pyridinyl)-3-methyl-1H-indol-1-amine (8.5 g) in 40 ml of DMF, when addition was complete, the mixture was stirred for 15 minutes at ice bath temperature, and then cooled to $-20°$ C. Ethyl chloroacetate (3.95 ml) was added dropwise in 10 ml of DMF. The mixture was stirred at $-20°$ C. for one hour. The mixture was then poured into water and extracted with ethyl acetate. The organic layer was washed with water and dried (sat. NaCl, anhy. $MgSO_4$). After filtering, the solvent was evaporated to yield an oil (12.2 g) which was eluted with 10% ethyl acetate/DCM on a silica gel column via HPLC. The desired fractions were evaporated to yield 6.9 g of a solid, m.p. 105°–108° C.

Analysis: Calculated for $C_{18}H_{18}FN_3O_2$: 66.04% C, 5.54% H, 12.84% N. Found: 66.00% C, 5.53% H, 12.81% N.

EXAMPLE 1c

N-(3-Fluoropyridin-4-yl)-N-(3-methyl-1H-indol-1-yl)-2-aminoethanol

To N-(3-fluoro-4-pyridinyl)-N-(3-methyl-1H-indol-1-yl)glycine ethyl ester (5.0 g) in 100 ml of tetrahydrofuran cooled to ice bath temperature was added lithium aluminum hydride (1M solution in tetrahydrofuran, 30 ml) via syringe. The reaction was stirred for 0.5 hour. The mixture was quenched with $NH_4Cl$ and extracted three times with ethyl acetate. The organics were combined, washed with sat. NaCl and dried ($MgSO_4$). After filtering, the solvent was evaporated to yield a solid (3.9 g) which was eluted with 50% ethyl acetate/dichloromethane on a silica gel column via high pressure liquid chromatography (HPLC). The desired fractions were evaporated to yield 3.7 g of a solid, m.p. 123°–125° C.

Analysis: Calculated for $C_{16}H_{16}FN_3O$: 67.35% C, 5.65% H, 14.73% N. Found: 67.45% C, 5.67% H, 14.72% N.

EXAMPLE 1d 4-(3-Methyl-1H-indol-1-yl)-pyrido[3,4-b]-1,4-oxazine

To a suspension of NaH (0.34 g) in 5 ml dimethylformamide was added N-(3-fluoro-pyridin-4-yl)-N-(3-methyl-1H-indol-1-yl)-2-aminoethanol (2.0 g) in 50 ml dimethylformamide. The reaction was heated to 70° C. and stirred for four hours. The mixture was poured into water and extracted with ethyl acetate. The organic layer was washed with water and dried (sat. NaCl, $MgSO_4$). After filtering, the solvent was evaporated to yield an oil (2.8 g), which was eluted with 50% ethyl acetate/dichloromethane on a silica gel column via HPLC. The desired fractions were evaporated to yield 1.0 g of a solid, m.p. 139°–141° C.

Analysis: Calculated for $C_{16}H_{15}N_3O$: 72.43% C, 5.70% H, 15.48% N, Found: 72.37% C, 5.74% H, 15.76% N.

EXAMPLE 2a

N-(3-Fluoro-4-pyridinyl)-N-(5-benzyloxy-1H-indol-1-yl)-2-aminoethanol

To a solution of N-(3-fluoro-4-pyridinyl)-N-(5-benzyloxy-1H-indol-1-yl)glycine ethyl ester (18.7 g) in 100 ml of tetrahydrofuran cooled to ice bath temperature, was added lithium aluminum hydride (89.16 ml) dropwise to the cool solution. The solution was stirred for 0.5 hour, then quenched with ammonium chloride and extracted with ethyl acetate. The organic layer was washed with water and dried (sat. NaCl, MgSO$_4$). After filtering, the solvent was evaporated to yield a solid (12.5 g) which was eluted with 50% ethyl acetate/dichloromethane on a silica gel column via HPLC. The desired fractions were evaporated to yield 9.65 g of a solid, m.p. 130°–132° C.

Analysis: Calculated for $C_{22}H_{20}FN_3O_2$: 70.01% C, 5.34% H, 11.13% N, Found: 69.98% C, 5.28% H, 11.04% N.

EXAMPLE 2b 4-(5-Benzyloxy-1H-indol-1-yl)-pyrido-[3,4-b]-1,4-oxazine

Sodium hydride (1.0 g) was suspended in dimethylformamide (10 ml) and this mixture cooled to ice bath temperature. A solution of N-(3-fluoro-4-pyridinyl)-N-(5-benzyloxy-1H-indol-1-yl)-2-amioethanol (8.25 g) in 100 ml of dimethylformamide was added dropwise, and the reaction mixture was then heated to 70° C. and stirred for three hours. The mixture was cooled, poured into water and extracted with ethyl acetate. The organic layer was washed with water and dried (sat. NaCl, anhy. MgSO$_4$). After filtering, the solvent was evaporated to yield a solid (12.2 g) which was eluted with 50% ethyl acetate/dichloromethane on a silica gel column via HPLC. The desired fractions were evaporated to yield 7.4 g of a solid, which was triturated with ether to yield 4.04 g of a solid, m.p. 181°–183° C.

Analysis: Calculated for $C_{22}H_{19}N_3O_2$: 73.93% C, 5.36% H, 11.75% N. Found: 73.67% C, 5.39% H, 11.68% N.

EXAMPLE 3

1-(Pyrido-[3,4-b]-1,4-oxazin-4-yl)-1H-indol-5-ol 4-(5-benzyloxy-1H-indol-1-yl)-pyrido-[3,4-b]-1,4-oxazine (5.0 g) in 240 ml of ethanol was added to a suspension of 10% Pd/C (0.6 g) in 10 ml of ethanol. This mixture was hydrogenated on a Parr apparatus for two hours at 50° C. The mixture was then cooled, filtered, and the filtrate evaporated to yield a solid (3.5 g). This material was eluted with 5% methanol/dichloromethane on a silica gel column via HPLC. The desired fractions were evaporated to yield 2.7 g of a solid. Of this material, 0.9 g was recrystallized from acetonitrile to yield 0.62 g of a solid, m.p. 221°–222° C.

Analysis: Calculated for $C_{15}H_{13}N_3O_2$: 67.40% C, 4.90% H, 15.72% N, Found: 67.38% C, 4.85% H, 15.68% N.

EXAMPLE 4

1-(Pyrido-[3,4-b]-1,4-oxazine-4-yl)-1H-indol-5-yl methylcarbamate

Potassium carbonate (1.3 g) was added to a solution of 1-(pyrido-[3,4-b]-1,4-oxazin-4-yl)-1H-indol-5-ol (2.0 g) in 100 ml of tetrahydrofuran. After stirring at room temperature for 10 minutes, methyl isocyanate (0.46 g) was added dropwise. The reaction was allowed to proceed for 1 hour at room temperature. The mixture was then filtered and the filtrate evaporated to yield a solid (2.8 g). This material was eluted with 5% methanol/dichloromethane of a silica gel column via HPLC. The desired fractions were evaporated to yield 3.2 g of a solid, which was recrystalized from acetonitrile to yield 1.5 g of a solid, m.p. 196°–198° C.

Analysis: Calculated for $C_{17}H_{16}N_4O_3$: 62.95% C, 4.97% H, 17.28% N, Found: 62.95% C, 4.91% H, 17.30% N.

EXAMPLE 5a

N-(3-Fluoro-4-pyridinyl)-N-(1H-indol-1-yl)glycine ethyl ester

To a suspension of sodium hydride (3.6 g) in 20 ml dimethylformamide at 0° C. was added a solution of N-(3-fluoro-4-pyridinyl)-1H-indol-1-amine (19 g) in 120 ml dimethylformamide over fifteen minutes, and the resultant mixture stirred at 0° C. for twenty minutes. After cooling the mixture to −20° C., a solution of ethyl chloroacetate (9.6 ml) in 25 ml dimethylformamide was added over fifteen minutes, and the resultant mixture stirred at −20° C. for one hour.

The mixture was poured into 400 ml water, stirred for five minutes, then extracted with ethyl acetate. The organic layer was washed with water and saturated NaCl solution, then dried over anhydrous MgSO$_4$.

After filtering, the solvent was evaporated to an oil (26 g) which was eluted on a silica gel column with 10% ethyl acetate/dichloromethane via HPLC. The desired fractions were combined, then evaporated to yield 13.3 g of N-(3-fluoro-4-pyridinyl)-N-(1H-indol-1-yl)glycine ethyl ester, as a solid, m.p. 86°–7° C.

Analysis: Calculated for $C_{17}H_{16}FN_3O_2$: 65.16% C., 5.15% H; 13.41% N. Found: 65.00% C, 5.14% H, 13.19% N.

EXAMPLE 5b

N-(3-Fluoropyridin-4-yl)-N-(1H-indol-1-yl)-2-aminoethanol

To a solution of lithium aluminum hydride (1M solution, 70 ml) cooled to 0° C., was added a solution of N-(3-fluoro-4-pyridinyl)-N-(1H-indol-1-yl)glycine ethyl ester (11.4 g) in 125 ml tetrahydrofuran in thirty minutes. After stirring at 0° C. for one hour, a solution of ammonium chloride was added, followed by 300 ml ethyl ether. The mixture was filtered, and the filtrate evaporated to a solid 10 g; which was eluted on a silica gel column with ethyl acetate/dichloromethane (1:1) via HPLC. The desired fractions were combined, then evaporated to yield 6.1 g of N-(3-fluoropyridin-4-yl)-N-(1H-indol-1-yl)-2-aminoethanol, as a solid, m.p. 133°–5° C.

Analysis: Calculated for $C_{15}H_{14}FN_3O$: 66.41% C, 5.20% H, 15.49% N. Found: 66.33% C, 5.22% H, 15.41% N.

EXAMPLE 5c

4-(1H-Indol-1-yl)-pyrido[3,4-b]-1,4-oxazine

To a suspension of sodium hydride (0.8 g) in 10 ml dimethylformamide, was added a solution of N-(3-fluoropyridin-4-yl)-N-(1H-indol-1-yl)-2-aminoethanol (4.8 g) in 100 ml dimethylformamide. After stirring at 70° C. for four hours, the mixture was poured into 300 ml ice-water, stirred for five minutes, then extracted with ethyl acetate. The organic layer was washed with water, then saturated NaCl solution and then dried over anhydrous MgSO$_4$.

After filtering, the solvent was evaporated to an oil, which was eluted on a silica gel column with ethyl acetate/dichloromethane (1:2) via HPLC. The desired fractions were combined then evaporated to a thick oil, which solidified on standing to yield 3.4 g of 4-(1H-indol-1-yl)-pyrido[3,4-b]-1,4-oxazine, as a solid, m.p. 108°–110° C.

Analysis: Calculated for C$_{15}$H$_{13}$N$_3$O: 71.70% C, 5.21% H, 16.72% N. Found: 71.38% C, 4.91% H, 16.52% N.

We claim:

1. A compound of the formula

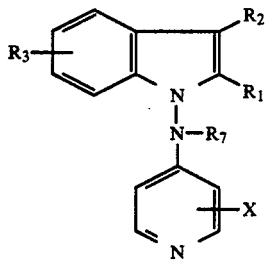

wherein
 R$_1$ is hydrogen or loweralkyl;
 R$_2$ is hydrogen or loweralkyl;
 R$_3$ is hydrogen, loweralkyl, halogen, nitro, amino, hydroxy, loweralkoxy, benzyloxy or

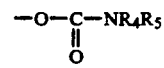

where R$_4$ is hydrogen or loweralkyl and R$_5$ is loweralkyl, aryl or arylloweralkyl, or R$_4$ and R$_5$ taken together form a heterocyclic ring selected from the group consisting of

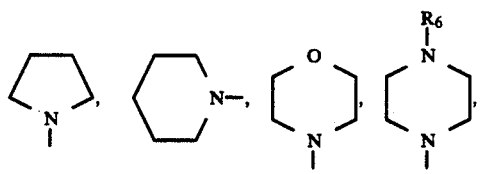

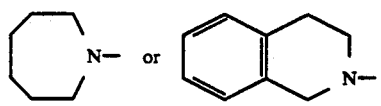

wherein R$_6$ is hydrogen, loweralkyl, aryl or aryl-loweralkyl; the term "aryl" in each occurrence signifying a phenyl group substituted with 0,1 or 2 substituents each of which being independently loweralkyl, loweralkoxy, halogen or trifluoromethyl; X is halogen, and R$_7$ is (CH$_2$)$_2$OH or

or a pharmaceutically acceptable addition salt thereof.

2. The compound as defined in claim 1 which is N-(3-fluoropyridin-4-yl)-N-(3-methyl-1H-indol-1-yl)-2-aminoethanol.

3. The compound as defined in claim 1 which is N-(3-fluoro-4-pyridinyl)-N-(5-benzyloxy-1H-indol-1-yl)-2-aminoethanol.

4. The compound as defined in claim 1 which is N-(3-fluoropyridin-4-yl)-N-(1H-indol-1-yl)-2-aminoethanol.

* * * * *